US005925776A

United States Patent [19]
Nikolayev et al.

[11] Patent Number: 5,925,776
[45] Date of Patent: Jul. 20, 1999

[54] POLYETHOXYLATED CASTOR OIL, PROCESS OF MAKING THE SAME AND FORMULATIONS THEREOF

[75] Inventors: Aleksandr Nikolayev, Maple Shade; Fakrul Sayeed, Voorhees; Rupa Iyer, Marlton; Mitchell Garber, Cherry Hill; Robert C. Butterhof, Southampton; Todd M. Hoyer, Trenton; Marvin Samson, Cherry Hill, all of N.J.

[73] Assignee: Schein Pharmacetical, Inc., Florham Park, N.J.

[21] Appl. No.: 08/998,306

[22] Filed: Dec. 24, 1997

[51] Int. Cl.$^6$ .......................... C07C 59/00; C07C 51/43; A01N 37/06
[52] U.S. Cl. .......................... 554/219; 514/549; 554/176
[58] Field of Search .................... 554/219, 176; 514/549

[56] References Cited

U.S. PATENT DOCUMENTS

| | | |
|---|---|---|
| 4,960,799 | 10/1990 | Nagy . |
| 5,015,744 | 5/1991 | Holton . |
| 5,407,683 | 4/1995 | Shively . |
| 5,415,869 | 5/1995 | Staubinger et al. . |
| 5,438,072 | 8/1995 | Bobee et al. ............ 514/449 |
| 5,462,726 | 10/1995 | Lodge . |
| 5,504,102 | 4/1996 | Agharkar et al. . |
| 5,681,846 | 10/1997 | Trissel . |

OTHER PUBLICATIONS

Engel et al, "High Performance Liquid Chromatographic Analysis (HPLC) and Human Pharmacokinetics of Taxol (NSC 125973)", Proc. of AACR, vol. 26, Mar. 1989, p.158, Abstract #625 pp. 59–64 (1991).
Kingston, David, "The Chemistry of Taxol", Pharmac. Ther. vol. 52, 1–34, 1991.
Kingston et al., "Synthesis and Structure—Activity Relationships of Taxol Derivatives as Anticancer Agents", New Trends in Natural Products Chemistry 1986, vol. 26, 219–235.
Richheimer et al., "High–Performance Liquid Chromatographic Assay of Taxol", Anal. Chem. 1992, vol. 64, 2323–2326.
Ringel et al., "Taxol is Converted to 7–Epitaxol, a Biologically Active Isomer, in Cell Culture Medium", Journal of Pharmacology and Experimental Therapeutics, vol. 242, 1987, 692–698.
Rizzo et al., "Analysis of anticancer drugs in biological fluids: determination of taxol with application to clinical pharmacokinetics", Journal of Pharmaceutical & Biomedical Analysis (1990), vol. 8(2), pp. 159–164.
Waugh et al., "Stability, compatability, and plasticizer extraction of taxol (NSC–125973) injection diluted in infusion solutions stored in various containers", AHJP vol. 48, Jul. 1991, 1520–1524.

Wiernik et al., "Phase I Trial of Taxol Given as a 24–Hour Infusion Every 21 Days: Response observed in Metastatic Melanoma", Journal of Clinical Oncology, vol. 5, No. 8, pp. 1232–1239 (Aug. 1987).
Chabner, "Taxol", Principles & Practice of Oncology (1991) 5:1–10 No. 9.
Collins–Gold et al., "Parenteral emulsions for drug delivery", Advanced Drug Delivery Reviews, 5 (1990) 189–208.
Donehower et al., "Phase I Trial of Taxol in Patients With Advanced Cancer", Cancer Treatment Reports vol. 71. No. 12, Dec. 1987, 1171–1177.
Einzig et al., "Phase II Trial of Taxol in Patients with Metastatic Renal Cancer Carcinoma", Cancer Investigation, 9(2) 133–136 (1991).
Einzig et al., "A phase II study of taxol patients with malignant melanoma", Investigational New Drugs 9, pp. 59–64 (1991).
Holmes et al., "Phase II Trial of Taxol, an Active Drug in the Treatment of Metastatic Breast Cancer", Journal of the National Cancer Institute 83:1797–1805 No. 24 (1989).
Kris et al., "Phase I Trial of Taxol Given as a 3–hour Infusion Every 21 Days", Cancer Treatment Reports, vol. 70, May 1986, pp.605–607.
Rose, William, "Taxol: a review of its preclinical in vivo antitumor activity", Anti–Cancer Drugs, vol. 3, 311–321, 1992.
Trissel et al., "compounding an Extended–Stability Admixture of Paclitaxel for Long–Term Infusion", International J. of Pharmaceutical Compounding, vol. 1, No. 1, Jan./Feb. 1997, pp. 49–53.
Room Temperature Stability of Taxol®, Bristol–Myers Squibb Oncology/Immunology—2 pages.
BASF, Products for the pharmaceutical Industry, Technical Information, ME 148 e (985) Nov. 1996 (JWF) pp. 1–15.
BASF, Cremophor® EL, Technical Leaflet, pp. 1–5.
BASF, Preliminary specification Cremophor® EL–P, Mar. 1995 (1 page).
Handbook of Pharmaceutical Excipients 1986 pp. 221–224.

*Primary Examiner*—Paul J. Killos
*Assistant Examiner*—J. Parsa
*Attorney, Agent, or Firm*—Irving M Fishman

[57] ABSTRACT

Polyethoxylated castor oil with a low cation content are claimed, along with particular methods for achieving such low cation content polyethoxylated castor oil. One method of production of such a low cationic content polyethoxylated castor oil according to the invention is to pre-treat the polyethoxylated castor oil with a strong cationic exchange resin to remove a substantial portion of the cations present in an untreated polyethoxylated castor oil. The low cationic content polyethoxylated castor oil of the invention can then be utilized to prepare formulations of various agents which are found to be sensitive to the previously commercially available polyethoxylated castor oil (CREMOPHOR EL®).

27 Claims, No Drawings

5,925,776

POLYETHOXYLATED CASTOR OIL, PROCESS OF MAKING THE SAME AND FORMULATIONS THEREOF

CROSS-REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

The invention relates to polyethoxylated castor oils. It also relates to ion-exchange methods for reducing metal cation. In addition, the invention relates to formulations, especially pharmaceutical formulations, of polyethoxylated castor oils. In preferred embodiments, the invention relates to antineoplastic formulations having the novel polyethoxylated castor oils.

BACKGROUND OF THE INVENTION

Polyethoxylated castor oil is a surfactant commonly used in a number of products for its emulsifying properties. In many contexts, it is a necessary agent to solubilize certain active agents, especially active agents which are only slightly or sparingly soluble in water. While the polyethoxylated castor oil is a suitable solubilizer for many agents, in a number of situations, those agents exhibit unacceptable degradation when the polyethoxylated castor oil is present.

One formulation containing polyethoxylated castor oil in which the active agent is degraded in the presence of polyethoxylated castor oil to a greater degree than in its absence is shown in U.S. Pat. No. 4,960,799, issued to Nagy on Oct. 2, 1990. In the invention there, the problem was stated as being solved by incorporation of a stabilizer, in particular, ethylene diamine tetraacetic acid (EDTA). EDTA is used in many aqueous pharmaceutical purposes, including as a sequesterant for multivalent ions.

In another pharmaceutical formulation, polyethoxylated castor oil is used as a solubilizer for a non-aqueous concentrate formulation of paclitaxel, which is, in use, diluted with either aqueous carrier for use as an infusion. Formulations prepared according to the label contents of this product using standard, commercially available, polyethoxylated castor oil (CREMOPHOR EL® available from BASF) and natural paclitaxel show fairly rapid degradation of the active moiety.

The currently U.S. marketed paclitaxel formulation (available from Bristol-Myers Squibb) does not show as rapid a degradation pattern as that observed with the formulations prepared above, but the Bristol-Myers Squibb product is formulated from semisyntheic active agent. Analysis of the Bristol-Myers Squibb product also revealed a reduced cation content relative to that of the formulation prepared above.

OBJECTS OF THE INVENTION

It is therefore an object of the invention, to provide a low-cationic content polyethoxylated castor oil for use in formulating various compositions, especially pharmaceuticals.

It is a further object of the invention to provide a process for the preparation of such a low-cationic content polyethoxylated castor oil.

It is still another object of the invention to provide pharmaceutical formulations containing polyethoxylated castor oil with improved stability against active agent degradation.

It is yet another object of the invention to provide a process for the production of improved formulations of polyethoxylated castor oil where the formulation has components which are sensitive to high cation content polyethoxylated castor oil'

Still another object of the invention is to provide a process for the production of pharmaceutical formulations (and the formulations themselves) of polyethoxylated castor oil having components which are sensitive to alkali metal cations.

Another object of the invention is to provide a process for the production of a formulation (and the formulation itself) of polyethoxylated castor oil together with components which are sensitive to alkaline earth metal cations.

A still further object of the invention is to provide a process for the production of a formulation (and the formulation itself) of polyethoxylated castor oil and components which are sensitive to certain multivalent cations.

Yet another object of the invention is to provide improved stability formulations of diclofenac.

Still another object of the invention is to provide improved stability formulations of paclitaxel.

Still other objects of the invention will be apparent to those of ordinary skill in the art.

BRIEF SUMMARY OF THE INVENTION

These and other objects of the invention can be realized by preparing formulations having polyethoxylated castor oil with a low cation content. For purposes of this invention, unless specifically set forth, cations present in the neat polyethoxylated castor oil of the invention below 2 ppm are ignored in the total cation content. The cations of interest in this invention include at least one of $NH_4$, Al, B, Ca, K, Mg, Na, Sn, and Zn (specific charges being omitted for convenience). One method of production of such a low cationic content polyethoxylated castor oil according to the invention is to pre-treat the polyethoxylated castor oil (preferably CREMOPHOR® EL, also known as poloxyl 35 castor oil) with a strong cationic exchange resin to remove a substantial portion of the cations present in an untreated or partially treated polyethoxylated castor oil. The low cationic content polyethoxylated castor oil of the invention can then be utilized to prepare formulations of various agents which were found to be sensitive to the previously commercially available polyethoxylated castor oil (CREMOPHOR EL®).

BRIEF DESCRIPTION OF THE SEVERAL VIEWS OF THE DRAWING

Not Applicable

DETAILED DESCRIPTION OF THE INVENTION

The present invention is primarily directed to:
1. low cationic content polyethoxylated castor oil;
2. low cationic content polyethoxylated castor oil containing formulations;
3. processes for the manufacture of low cationic content polyethoxylated castor oil;
4. processes for the manufacture of formulations containing low cationic content polyethoxylated castor oil;
5. methods of use of low cationic content polyethoxylated castor oil;

6. low cationic content polyethoxylated castor oil obtained by the process of the invention; and
7. formulations of low cationic content polyethoxylated castor oil obtained by the process of the invention.

The low cationic content polyethoxylated castor oil of the present invention has a content of at least one of the following cations present in an amount of not more than about the stated amount in the table below, based on the total neat polyethoxylated castor oil content (inclusive of such cations).

| | AMOUNT (PPM) (not more than about) | | |
|---|---|---|---|
| CATION | GENERALLY | PREFERABLY | MORE PREFERABLY |
| $NH_4$ | 50 | 40 | 30 |
| Al | 20 | 10 | 4 |
| B | 20 | 15 | 10 |
| Ca | 80 | 50 | 24 |
| K | 20 | 15 | 6 |
| Mg | 6 | 4 | 2 |
| Na | 50 | 24 | 12 |
| Sn | 6 | 4 | 2 |
| Zn | 21 | 18 | 14 |

Preferably, the low cationic content polyethoxylated castor oil of the present a invention (hereinafter the "lcp-castor oil") has an alkali metal cation content (based on the neat polyethoxylated castor oil inclusive of all cations present) of not more than about 200 ppm, more preferably not more than about 120 ppm, still more preferably not more than about 60 ppm, even more preferably mot more than about 40 ppm, most preferably not more than about 20 ppm.

Preferably, the lcp-castor oil has an alkaline earth metal cation content (based on neat polyethoxylated castor oil inclusive of all cations present) of not more than about 200 ppm, more preferably not more than about 120 ppm, still more preferably not more than about 90 ppm, still more preferably not more than about 60 ppm, most preferably not more than about 30 ppm.

Preferably, the lcp-castor oil has a multivalent (2 or more charges) cation content (based on neat polyethoxylated castor oil inclusive of all cations which are present) of not more than about 200 ppm, more preferably not more than about 160 ppm, still more preferably not more than about 110 ppm, most preferably not more than about 60 ppm.

In highly preferred embodiments, the lcp-castor oil of the invention has a content (based on neat polyethoxylated castor oil inclusive of all which are present) of no more than about:

| | AMOUNT (PPM) (not more than about) | | |
|---|---|---|---|
| CATION | GENERALLY | PREFERABLY | MORE PREFERABLY |
| $NH_4$ | 50 | 40 | 30 |
| Ca | 80 | 50 | 24 |
| K | 20 | 25 | 6 |
| Na | 50 | 24 | 12 |

The lcp-castor oil of the present invention has a pH of less than about 5.0, preferably less than about 4.7, more preferably less than about 4.4, most preferably less than about 4.2 when measured under the following conditions:

527 parts by weight of the lcp-castor oil of the invention is dissolved in sufficient dehydrated alcohol to result in a solution of 527 mg/ml of solution. An aliquot of solution is diluted with 13.29 times the aliquot weight of water and the pH of the aqueous solution is measured.

The lcp-castor oil is prepared by the method of the present invention set forth below generally utilizing as a starting material commercially available polyethoxylated castor oil available from BASF under the name CREMOPHOR®. Two currently available grades which are extremely useful in the present invention are CREMOPHOR® EL and CREMOPHOR® EL-P. Other polyethoxylated castor oils available from BASF and others are also suitable for use in the present invention; however, CREMOPHOR® EL has been the preferred polyethoxylated castor oil used in pharmaceutical formulations. It should be recognized that the particular polyethoxylated castor oil for use in the present invention is only limited by the ultimate use for which one wishes to use the material, i.e. pharmaceuticals, cosmetics, feedstuff, industrial applications, etc.

The lcp-castor oil is prepared by the process of the present invention generally by preferably exposing the polyethoxylated starting material to a cationic exchange resin. Preferably, the cationic exchange resin is a strong cationic exchange resin (as that term is generally understood in the art with respect to use of cationic exchange resins when used with aqueous solutions). Mixtures of cationic exchanges resins may be used without departing from the invention, although the efficiency of the exchange may be hindered if too much weak cationic exchange resin is present. Mixtures of cationic and anionic exchange resins are also possible, but inclusion of anionic exchange resins will detract from the efficiency of the process and is generally less preferable.

While any cationic exchange resin is suitable for use in the present invention process, as stated above, a strong cationic exchange resin is preferred. Most preferably the exchange resin is a sulfated styrene divinyl benzene resin. Of these, Dowex Monosphere 650c (available from Dow Chemical) is most preferred. Other cationic exchange resins suitable for use in the present invention will be known to those of ordinary skill in the art.

Preferably the exchange resin is substantially free of water during the contact time with the polyethoxylated castor oil; most preferably it is water-free. For purposes of the present invention, the resin is defined as being water-free when it has a water content at or below that level achieved from oven drying to constant weight at about 50° C. (45° C.–55° C.). Also, it is preferable that the polyethoxylated castor oil starting material be substantially water free (i.e., no more than about 1% water, preferably no more than about 0.6% water), and most preferably it is water-free, when introduced to the cationic exchange resin. Preferably, the substantially water-free natures of the of the polyethoxylated castor oil and the cationic exchange resin are maintained throughout the contact time between the polyethoxylated castor oil and the exchange resin. The resin and the polyethoxylated castor oil starting material can be dried to a substantially (i.e. generally less than about 1.0%) or totally water-free state using techniques well known in the art.

In order to contact the polyethoxylated castor oil starting material with the exchange resin, a suitable solvent is needed. Preferably, the solvent is substantially water free, most preferably it is water-free. The solvent is selected from polar and non-polar solvents in which the polyethoxylated castor oil will dissolve. These will generally be known in the art or readily determined by consulting the polyethoxylated castor oil's manufacturer's product literature or conducting simple dissolution tests. Preferably the solvent is a low molecular weight alcohol such as methanol, ethanol, propanol, isopropanol, or butanol; more preferably ethanol or isopropanol, most preferably ethanol. Commercially available dehydrated ethanol is especially useful.

The polyethoxylated castor oil starting material (preferably after drying to a suitable state) is mixed with the (preferably dried) solvent and the mixture (solution) is contacted with the pre-dried cationic exchange resin. If either the starting material or the solvent has not been previously dried to the requisite water content, the solution can be further dried to suitable levels. The substantially water-free polyethoxylated castor oil/solvent solution is introduced to the cationic exchange resin which may be used in a column or in a slurry bed form as is known in the art.

The contact time between the polyethoxylated castor oil starting material and the exchange resin will vary with the strength of the exchange resin and the capacity of the exchange resin in a manner which will readily be appreciated by those of ordinary skill in the art. In general, when Dowex Monosphere 650c is used a s the exchange resin, CREMOPHOR EL is the starting polyethoxylated castor oil and dehydrated alcohol is used as the solvent in a slurry contact method, and the resin to polyethoxylated castor oil to be treated is about 1:9, the contact time between the polyethoxylated castor oil and the exchange resin is maintained for a period of about 2 hours and completion of the exchange process is monitored until a pH of less than about 5.0, preferably less than about 4.7, more preferably less than about 4.4, most preferably less than about 4.2, for at least three consecutive samplings taken at least 20 minutes, preferably at least 25 minutes, more preferably at least 30 minutes apart, with the first sampling being taken after at least 45 minutes, preferably after about 1 hour of contact time. Based on these parameters, those of ordinary skill in the art will be able to modify each of contact time, resin capacity, resin strength, solvent, and the particular polyethxylated castor oil and remain within the present invention.

After the contact time is completed, the solution is separated from the resin in manners which are well known in the art. Additional dried solvent can be utilized to wash the resin slurry or elute any residual material from the column. The recovered lcp-castor oil may be used as is (i.e. in the recovered solution) or the solution solvent may be removed in generally known techniques to obtain substantially solvent-free or solvent-free lcp-castor oil. Generally, where the solvent used is not problematical to the ultimate use for which the lcp-castor oil is desired, the solution recovered from the ion exchange process will be used directly.

The obtained lcp-castor oil (whether or not in solution) may then be used to prepare formulations of various materials as is known in the art for the starting polyethoxylated castor oil. In addition, formulations of the starting polyethoxylated castor oil which required certain stabilizers, which may have their own drawbacks, can now be formulated without such stabilizers or with substantially lower amounts of such stabilizers. In addition, the present invention lcp-castor oil now allows for formulating various active agents which were intolerant to the known polyethoxylated starting materials with the lcp-castor oil to take advantage of polyethoxylated castor oil emulsifying and solubilizing properties.

It should be noted that the invention process reduces the content of a number of cations found in currently commercially available polyethoxylated castor oil. When one utilizes the present invention lcp-castor oil, it is preferable to avoid reintroduction of these cations in the formulation process. However, if it is known or determined that only a subgroup of cations is problematical, then the reintroduction of the remaining cations not in that particular subgroup may take place without departing from the invention. Simple determinations of which cations are or are not problematical in a particular formulation can be made by preparing the formulation without reintroduction of such cations and spiking a sample with that cation and comparing the stability of the formulations.

Particular formulation components with which the lcp-castor oil (per se or as dissolved in the solvent) may be formulated include, without limitation:

1. Active Agents pharmaceutically active agents such as: vitamins such as A, D, E, and K; essential oils (i.e. flavors and fragrances); anesthetics such as benzocaine; antifungals such as miconazole and clotrimazole; antibacterials such as hexidine; non-steroidal anti-inflammatory agents such as diclofenac; antitumor agents such as paclitaxel; deodorant and antiperspirant actives such as aluminum zirconium chloride, aluminum chloride, sodium bicarbonate, etc.; among others. Particularly preferred active agents include diclofenac and paclitaxel. A most preferred embodiment of the use of the lcp-castor oil is for formulating paclitaxel.

and 2. excipients such as solvents, thickeners, colors, dyes, flow aids, lubricants, non-volatile silicones such as cyclomethicone, clays such as bentonites, etc.

When paclitaxel is the active agent, the concentrate is generally diluted to about 0.3 to about 1.2 mg paclitaxel per ml. The diluent can be selected from any physiologically acceptable diluent including but not limited to isotonic saline, isotonic dextrose, Ringers solution, as well as various mixtures thereof. In addition, the pH of the dilute solution may be adjusted toward physiologic pH with various buffers and/or bases known to be acceptable for intravenous infusion. The buffers and/or bases may be incorporated into the diluent prior to dilution of the concentrate. While it is important to restrict the cation content of the concentrate, the 0.3 to 1.2 mg per ml solution is generally used within about 30 hours, preferably within about 25 hours of preparation, and therefore may contain cations substantially in excess of the limits set forth for the lcp-castor oil and for the paclitaxel concentrate above.

EXAMPLES

The forgoing invention will be more clearly seen and understood with reference to the following examples, which merely exemplify, but do not limit, the invention as claimed in the claims set forth below.

Example I

Unless specifically stated otherwise, amounts of materials used, whether weight or volume, are measured at room temperature.

Resin

Styrene divinyl benzene resin (Dowex 650c nuclear grade, available from Dow Chemical) is obtained in the protonated form as beads. The raw beads are prepared for use by wetting the beads in a column with water for injection and then washing the column, first with 4% sodium hydroxide solution (in water for injection), followed by plain water for injection, then 5% HCl in water for injection, then once more with water for injection, and finally by 5% HCl in water for injection followed by water for injection rinses (2). The washed resin is then dried at about 50° C. to constant weight to obtain the prepared resin.

The dried resin is then swelled by adding sufficient dehydrated alcohol to the dried resin to effect swelling. An initial aliquot of dehydrated alcohol is used which is at least equal in volume to the resin, with more dehydrated alcohol being added to keep all of the resin covered by the dehydrated alcohol for a period of about 2 hours. The alcohol is then drained from the resin beads.

Polyethoxylated Castor Oil

CREMOPHOR® EL (polyethoxylated castor oil obtained from BASF) is sparged under dry nitrogen and heated at about 50° C. (45° C.–55° C.) until the water content is not greater than 0.6%.

Cation Exchange

For every 100 grams of CREMOPHOR® EL used above, 74.3 grams of dehydrated alcohol is added to the dried CREMOPHOR® EL, followed by 9.35 ml of the drained resin beads with agitation. Mixing is continued for 1 hour after which pH is measured by the procedure set forth below. Additional pH measures are made every 30 minutes thereafter until at least three measures are consistently below about 4.2. The solution is decanted and filtered to recover the low cation content polyethoxylated castor oil in dehydrated alcohol. The solution is then optionally subjected to solvent removal by sparging with dry nitrogen while heating to approximately 50° C. to yield the substantially solvent free material.

pH Measurement

The pH measurements indicated above are conducted by removing an aliquot of solution, taking care not to remove any resin. 13.29 times the aliquot weight of water is added and the pH of the aqueous solution is measured.

Example II

Example I is repeated starting with CREMOPHOR® EL-P (available from BASF) in place of the CREMOPHOR® EL used in Example I.

Example III

The treated CREMOPHOR® EL of Example I, and the treated CREMOPHOR® El-P of Example II, and commercially available Taxol (527 mg/ml CREMOPHOR, 6 mg/ml paclitaxel, and dehydrated alcohol 49.7 v/v % of the solution) were analyzed for the following cations. The amounts reported below are from solutions of the respective polyethoxylated castor oil (527 mg/ml) in dehydrated alcohol (49.7 v/v % of the final solution) and are based on the entire solution.

| Cation Content in Parts Per Million of Solution | | | |
|---|---|---|---|
| Cation | material of Example I | material of Example II | Taxol |
| Al | 2 | 1 | 38 |
| B | 1 | <1 | 3 |
| Ca | 12 | 7 | 4 |
| K | 3 | 2 | 1 |
| Mg | <1 | <1 | <1 |
| Na | 6 | 4 | 26 |
| Sn | <1 | 1 | 6 |
| Zn | 7 | 1 | <1 |

Example IV

A diclofenac formulation utilizing the substantially solvent free low cation content polyethoxylated castor oil produced in Example I is prepared as follows. Under nitrogen flush, 9 mls of water are added to a vessel. The following ingredients are added to the vessel, in sequence, in the amounts given, with stirring until each is dissolved before the next is added.

| | |
|---|---|
| lcp-castor oil | 250.0 mg |
| sodium phosphate monobasic | 36.8 mg |
| sodium phosphate dibasic | 109.2 mg |
| thimerosal | 0.4 mg |
| mannitol | 89.0 mg |
| diclofenac sodium | 10.0 mg |
| water | q.s. to 10 ml |

Examples V–VII

A paclitaxel (an antitumor drug) formulation having polyethoxylated castor oil as a solubilizer for the paclitaxel is prepared as follows:

To a given amount of polyethoxylated castor oil in dehydrated alcohol, paclitaxel is added with stirring in accordance with the formula below.

| | |
|---|---|
| polyethoxylated castor oil | 527 mg/ml of final solution |
| dehydrated alcohol | 49.7 v/v % of final solution |
| paclitaxel | 6 mg/ml of final solution | using the following polyethoxylated castor oils:

| Example | Polyethoxylated Castor Oil |
|---|---|
| V | CREMOPHOR ® EL-P |
| VI | material from Example I |
| VII | commercially available Taxol |

Each of the three formulations above were put on accelerated stability and tested at various points for the presence of paclitaxel as well as for the presence of Baccatin III and 7-epipaclitaxel (two known degradation products of paclitaxel). The results are set forth below in Tables I–III.

TABLE I

BACCATIN III

| Sample Time | Example V (CREMOPHOR) | Example VI (invention) | Example VII (Commercial Taxol) |
|---|---|---|---|
| initial | 0.01 | <lod | |
| 5 days at 60° C. | | | 0.05 |
| 12 hrs at 60° C. | 9.16 | | |
| 1 wk at 60° C. | | 0.02 | |
| 4 wk at 60° C. | | 0.12 | |
| 3 wk at 40° C. | | | 0.04 |
| 4 wk at 40° C. | 4.23 | 0.02 | |
| 3 wk at 25° C. | | | 0.03 |
| 4 wk at 25° C. | 0.83 | <lod | |

TABLE II

7-EPIPACLITAXEL

| Sample Time | Example V (CREMOPHOR) | Example VI (invention) | Example VII (Commercial Taxol) |
|---|---|---|---|
| initial | 0.06 | 0.07 | |
| 12 hrs at 60° C. | 2.52 | | |
| 5 days at 60° C. | | | 0.07 |
| 1 wk at 60° C. | | 0.09 | |

TABLE II-continued

7-EPIPACLITAXEL

| Sample Time | Example V (CREMOPHOR) | Example VI (invention) | Example VII (Commercial Taxol) |
|---|---|---|---|
| 4 wk at 60° C. |  | 0.14 |  |
| 3 wk at 40° C. |  |  | 0.03 |
| 4 wk at 40° C. | 0.61 | 0.08 |  |
| 3 wk at 25° C. |  |  | 0.02 |
| 4 wk at 25° C. | 0.13 | 0.07 |  |

TABLE III

CHROMATOGRAPHIC PURITY OF PACLITAXEL

| Sample Time | Example V (CREMOPHOR) | Example VI (invention) | Example VII (Commercial Taxol) |
|---|---|---|---|
| initial | 99.7 | 99.5 |  |
| 5 days at 60° C. |  |  | 98.9 |
| 12 hrs at 60° C. | 87.3 |  |  |
| 1 wk at 60° C. |  | 99.4 |  |
| 4 wk at 60° C. |  | 99.1 |  |
| 3 wk at 40° C. |  |  | 99.2 |
| 4 wk at 40° C. | 94.6 | 99.4 |  |
| 3 wk at 25° C. |  |  | 99.2 |
| 4 wk at 25° C. | 98.7 | 99.5 |  |

These results show that treatment of CREMOPHOR EL according to the invention and formulated with paclitaxel in accordance with the labeling for commercially available Taxol injection results in a product which is more stable than either the commercially available Taxol or the corresponding product formulated from the high purity CREMOPHOR EL-P (untreated). The paclitaxel product made in accordance with the invention can be suitably stored up to at least 30° C. without difficulty; refrigeration while advantageous is not necessary.

We claim:

1. A low cation content polyethoxylated castor oil (lcp-castor oil) having at least an Al, K, and Na cation content no greater than the respective amount set forth below:

| Cation | ppm |
|---|---|
| Al | 20 |
| K | 20 |
| Na | 12 and |
| Ca | 80 | based on neat lcp-castor oil.

2. The lcp-castor oil of claim 1 wherein said Al, K, and Na cation content is no greater than that set forth below:

| Cation | ppm |
|---|---|
| Al | 4 |
| K | 6 |
| Na | 12 and |
| Ca | 80 | based on neat lcp-castor oil.

3. The lcp-castor oil of claim 1 having at least one additional cation selected from the group comprising $NH_4$, B, Mg, Sn, and Zn present in an amount of no greater than that set forth below:

| Cation | ppm |
|---|---|
| $NH_4$ | 50 |
| B | 20 |
| Mg | 6 |
| Sn | 6 |
| Zn | 21 | based on neat lcp-castor oil.

4. The lcp-castor oil of claim 2 having at least one additional cation selected from the group comprising $NH_4$, B, Mg, Sn, and Zn present in an amount of no greater than that set forth below:

| Cation | ppm |
|---|---|
| $NH_4$ | 30 |
| B | 10 |
| Mg | 2 |
| Sn | 2 and |
| Zn | 14 | or said calcium ion content is not in excess of 24 ppm, base on neat lcp-castor oil.

5. A method of using the lcp-castor oil of claim 1 comprising dissolving the lcp-castor oil of claim 1 in sufficient dehydrated alcohol and adding thereto a sufficient amount of paclitaxel to arrive at a formulation having per ml, about 527 mg of the lcp-castor oil of claim 1, about 6 mg of paclitaxel, and about 49.7 v/v % dehydrated alcohol.

6. The lcp-castor oil of claim 3 wherein Ca is present in amounts not in excess of that stated in claim 3.

7. The lcp-castor oil of claim 3 wherein both Ca and Mg are present in amounts not greater than that stated in claim 3.

8. The lcp-castor oil of claim 3 wherein each of the cations selected from $NH_4$, Al, B, Ca, Mg, Na, and Zn is present in amounts not in excess of that stated in claim 3.

9. The lcp-castor oil of claim 1 having a pH of not greater than about 5.0 measured when 527 mg of the neat lcp-castor oil is dissolved in sufficient dehydrated alcohol to make 1 ml of solution and the resultant solution is diluted with 13.29 times the weight of such solution of water.

10. A stabilized formulation of a polyethoxylated castor oil comprising the lcp-castor oil of claim 1.

11. A stabilized formulation of a polyethoxylated castor oil comprising the lcp-castor oil of claim 3.

12. A stabilized formulation of a polyethoxylated castor oil comprising the lcp-castor oil of claim 4.

13. The formulation of claim 10 having an active agent selected from diclofenac and paclitaxel.

14. The formulation of claim 13 wherein paclitaxel is the active agent.

15. The formulation of claim 14 comprising per ml of solution, about 527 mg of the lcp-castor oil, about 6 mg of paclitaxel, and about 49.7 v/v % dehydrated alcohol.

16. A process for the manufacture of an lcp-castor oil of claim 3 comprising exposing an untreated or partially treated polyethoxylated castor oil to an activated cationic exchange resin in a solvent for said polyethoxylated castor oil for a sufficient time to reduce the cation metal content thereof to result in the lcp-castor oil of claim 3.

17. The process of claim 16 said untreated or partially treated polyethoxylated castor oil and said solvent are substantially water-free.

18. The process of claim 17 wherein said substantially water-free polyethoxylated castor oil has a water content of not greater than about 1% and said dehydrated alcohol has a water content of not greater than about 1%.

19. The process of claim 16 wherein said cation exchange resin is styrene divinyl benzene resin.

20. The process of claim 19 wherein said exchange resin is used in an amount in proportion to said polyethoxylated castor oil of about 1 part resin to 9 parts of polyethoxylated castor oil.

21. The process of claim 20 wherein said exposing step is for a period of not less than about 1 hour 25 minutes with a monitoring of the pH of the solution after at least 45 minutes and the exposing step continuing until at least three consecutive pH readings taken at least 20 minutes apart show a pH of not greater than about 5.0 when measured by diluting a portion of the polyethoxylated castor oil in dehydrated alcohol solution with 13.29 times (by weight) as much water.

22. A process for the manufacture of stabilized formulations of polyethoxylated castor oil comprising obtaining the lcp-castor oil of claim 1, combining said lcp castor oil with a suitable active agent and at least one carrier.

23. A method of using the lcp-castor oil of claim 1 comprising preparing stable formulations of active agents therewith.

24. A low cation content polyethoxylated castor oil obtained from the process of claim 16.

25. A formulation of a low cation content polyethoxylated castor oil comprising the low cation content polyethoxylated castor oil of claim 24, an active agent, and a carrier therefor.

26. The formulation of claim 25 wherein said carrier is a solvent.

27. The formulation of claim 26 wherein said carrier is dehydrated alcohol and said active agent is paclitaxel.

* * * * *

UNITED STATES PATENT AND TRADEMARK OFFICE
CERTIFICATE OF CORRECTION

PATENT NO. : 5,925,776
DATED : July 20, 1999
INVENTOR(S) : Nikolayev, et. al.

It is certified that error appears in the above-identified patent and that said Letters Patent is hereby corrected as shown below:

On the Cover Page, in the recitation of U.S. PATENT DOCUMENTS, insert

--5,653,972 8/97 Desai--

On the Cover Page, before the line "OTHER PUBLICATIONS", insert

--FOREIGN PATENT DOCUMENTS

EP 645,145 3/95 Agharkar-- and

On the cover Page, after the last entry under "OTHER PUBLICATIONS", insert

--Kirk Othmer, Encyclopedia of Chemical Technology, Third Edition, Volume 13, pp. 6787-694.--

Claim 1, at Column 9, line 41, after "K," insert --Ca,--.

Claim 2, at Column 9, line 52, after "K," insert --Ca,--.

Claim 4, at Column 10, line 23, change "base" to --based--.

Signed and Sealed this

Fourth Day of April, 2000

Attest:

Q. TODD DICKINSON

Attesting Officer

Director of Patents and Trademarks